United States Patent [19]  [11] 3,994,878
Partridge, Jr. et al.  [45] Nov. 30, 1976

[54] SYNTHESES OF 24R,25- AND 24S,25-DIHYDROXYCHOLESTEROL AND ALKANOYL DERIVATIVES THEREOF

[75] Inventors: John Joseph Partridge, Jr.; Milan Radoje Uskokovic, both of Upper Montclair, N.J.

[73] Assignee: Hoffmann-La Roche Inc., Nutley, N.J.

[22] Filed: Oct. 10, 1975

[21] Appl. No.: 621,319

[52] U.S. Cl. ................... 260/239.55 R; 260/397.2
[51] Int. Cl.² ........................................... C07J 21/00
[58] Field of Search ................................ 260/397.2

[56] References Cited
UNITED STATES PATENTS 3,822,254   7/1974   Partridg, Jr. et al. ...... 260/239.55 R
3,928,397   12/1975   Ikekawa et al. .................. 260/397.2

OTHER PUBLICATIONS

Seki et al., "Tetrahedron Letters", (1975), No. 15, Jan. pp. 15–18.

Primary Examiner—Elbert L. Roberts
Attorney, Agent, or Firm—Samuel L. Welt; George M. Gould; Raymond R. Wittekind

[57] ABSTRACT

Syntheses of 24R- and 24S,25-dihydroxycholesterol and alkanoyl derivatives thereof, intermediates in the preparation of biologically important metabolites of vitamin $D_3$, are described.

45 Claims, No Drawings

SYNTHESES OF 24R,25- AND 24S,25-DIHYDROXYCHOLESTEROL AND ALKANOYL DERIVATIVES THEREOF

BACKGROUND OF THE INVENTION

The isolation and characterization of 24,25-dihydroxycholecalciferol (24,25-dihydroxyvitamin $D_3$) (M. F. Holick et al., Biochemistry, II, 4251 [1972]), and the subsequent finding that this second most abundant metabolite of vitamin $D_3$ (J. L. Omdahl and H. F. DeLuca, Physiological Reviews, 53, 327 [1973]) preferentially stimulates intestinal calcium transport without, at comparable dose levels, mobilizing bone calcium and is biologically synthesized in the kidney at the expense of the production $1\alpha,25$-dihydroxycholecalciferol, the potent, rapid-acting, natural metabolite of vitamin $D_3$ (J. L. Omdahl and H. F. DeLuca, supra), prompted fairly extensive investigation of the physiological role played by this metabolite (see for example, H. K. Schnoes and H. F. DeLuca, Vitamins and Hormones, 32, 395 [1974]). These investigations have been hampered by the minute amounts of the metabolite available from natural sources, the lack of information concerning the stereochemistry of the metabolic hydroxyl group at C-24 and the effect of the configuration of this group on the biological activity exhibited by 24,25-dihydroxycholecalciferol.

Recently, M. Seki et al. (Chem. Pharm. Bull. [Japan], 21, 2783 [1973]) described the non-stereoselective conversion of demosterol acetate to $24\xi,25$-dihydroxycholesterol by either epoxidation with m-chloroperbenzoic acid followed by hydrolysis or hydroxylation with osmium tetroxide followed by reductive hydrolysis. The diol of undefined stereochemical composition at C-24, as well as the epoxide, were subsequently used for the preparation of 24R,25- and 24S,25-dihydroxycholecalciferol in a process which involves separation of the epimeric 24,25-epoxides or 24,25-diols followed by the established steps for the conversion of cholesterol derivatives to vitamin $D_3$ metabolites. Shortly thereafter, H. -Y. Lam et al. (Biochemistry, 12, 4851 [1973]) reported a non-stereoselective synthesis of $24\xi,25$-dihydroxycholecalciferol starting from $3\beta$-acetoxy-27-nor-5-cholesten-25-one and proceeding via 24,25-dihydroxycholesterol. J. Redel et al. (Compt. rend. Acad. Sci. [Paris], 278, 529 [1974]) disclosed a non-stereoselective process for the preparation of the vitamin $D_3$ metabolite. The latter process started with desmosterol acetate, proceeded through an undetermined mixture of 24R,25- and 24S,25-dihydroxycholesterols and gave an extremely poor (about 1%) yield of an undefined mixture of 24R,25- and 24S,25-dihydroxycholecalciferol. Thus stereospecific synthesis of 24R- and 24S,25-dihydroxycholecalciferol utilizing 24,25-dihydroxycholesterol derivatives of known stereochemistry at C-24 overcoming the deficiencies of the prior art processes and making this important metabolite of vitamin $D_3$ readily available for biological, clinical and therapeutic use would represent a major contribution to the advancement of the state of the art in the vitamin D field.

DETAILED DESCRIPTION OF THE INVENTION

The present invention relates to a novel, efficient process for the preparation of 24R,25- and 24S,25-dihydroxy-$6\beta$-hydroxy or substituted $6\beta$-hydroxy-$3\alpha,5$-cyclo-$5\alpha$-cholest-24-ene, which is readily obtainable from the naturally occurring (readily available and relatively inexpensive) stigmasterol. More particularly, the present invention relates to a method for synthesizing 24R,25- and 24S,25-dihydroxy-$6\beta$-hydroxy or substituted $6\beta$-hydroxy-$3\alpha,5$-cyclo-$5\alpha$-cholestane comprising the key steps of hydroxylating $6\beta$-hydroxy or substituted $6\beta$-hydroxy-$3\alpha,5$-cyclo-$5\alpha$-cholest-24-ene to a mixture of 24R,25- and 24S,25-dihydroxy-$6\beta$-hydroxy or substituted $6\beta$-hydroxy-$3\alpha,5$-cyclo-$5\alpha$-cholestanes, separating the mixture of isomers, separately selectively converting each isomer to 25-hydroxy-$6\beta$-hydroxy- or substituted $6\beta$-hydroxy-24R- or 24S-lower alkyl- or lower alkylphenylsulfonyloxy-$3\alpha,5$-cyclo-$5\alpha$-cholestane, separately stereospecifically cyclizing each isomer to 24R,25- or 24S,25-epoxy-$6\beta$-hydroxy or substituted $6\beta$-hydroxy-$3\alpha,5$-cyclo-$5\alpha$-cholestane and separately stereospecifically cleaving the epoxy group of each isomer to 24R,25- and 24S,25-dihydroxy-$6\beta$-hydroxy or substituted $6\beta$-hydroxy-$3\alpha,5$-cyclo-$5\alpha$-cholestane.

As used throughout the specification and the appended claims, the term alkyl group refers to a monovalent substituent consisting solely of carbon and hydrogen of from 1 to 20 carbon atoms which may be straight or branched-chain. Examples of alkyl groups are methyl, ethyl, n-propyl, i-propyl, tert-butyl, hexyl, octyl, and so forth. The term alkylene group refers to a divalent substituent consisting solely of carbon and hydrogen of from 1 to 20 carbon atoms which may be straight or branched-chain and whose free valences are attached to two distinct groups. Examples of alkylene groups are methylene, ethylene, propylene and so forth. The term alkoxy group refers to a monovalent substituent which consists of an alkyl group linked through an ether oxygen having its free valence bond from the ether oxygen. Examples of alkoxy groups are methoxy, ethoxy, isopropoxy, tert-butoxy and so forth. The term phenyl alkoxy refers to an alkoxy group which is subsituted by a phenyl ring. Examples of phenyl alkoxy groups are benzyloxy, 2-phenylethoxy, 4-phenylbutoxy and so forth. The term alkanoyloxy group refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and so forth. The term substituted as applied to phenyl refers to phenyl which is substituted with one or more of the following groups: alkyl, halogen (i.e., fluorine, chlorine, bromine or iodine), nitro, cyano, trifluoromethyl and so forth. The term lower as applied to any of the aforementioned groups, refers to those groups having from 1 to 8 carbon atoms.

In the formulas presented herein, the various substituents are illustrated as joined to the steroid nucleus by one of these notations: a solid line ( — ) indicating a substituent which is in the $\beta$-orientation (i.e., above the plane of the molecule), a dotted line (-----) indicating a substituent which is in the $\alpha$-orientation (i.e., below the plane of the molecule), or a wavy line (~) indicating a substituent which may be in the $\alpha$- or $\beta$-orientation. The formulas have all been drawn to show the compounds in their absolute stereochemical configurations. Since the starting material, $6\beta$-hydroxy or substituted $6\beta$-hydroxy-$3\alpha,5$-cyclo-$5\alpha$-cholest-24-ene, is derived from naturally occurring stigmasterol, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively. Optically active products can then be prepared by resolution of the racemic products utilizing in the preparation thereof standard resolution techniques well known in the steroid art.

The Greek letter xi ($\xi$) in the name of a vitamin $D_3$ intermediate or metabolite indicates that the stereochemistry of the substituent to which it refers is undefined.

The nomenclature adopted to define absolute configuration of substituents bound to carbon atom 24 of the steroid nucleus is described in the Journal of Organic Chemistry, 35, 2849 (1970) under the title "IUPAC Tentative Rules for the Nomenclature of Organic Chemistry. Section E. Fundamental Stereochemistry". For example, since the handedness of the sequence rule-preferred group bound to carbon atom 24 in compound II is counterclockwise, the absolute stereochemistry is denoted by the prefix R.

The starting material, a compound of the formula

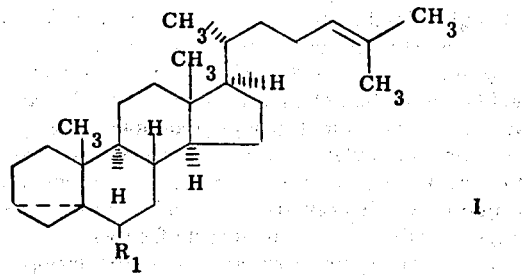

I wherein $R_1$ is hydroxy, lower alkoxy, phenyl lower alkoxy, lower alkanoyloxy or benzoyloxy for the preparation of 24R,25- and 24S,25-dihydroxy-6β-hydroxy or substituted 6β-hydroxy-3α,5-cyclo-5α-cholestane is synthesized by the process described in U.S. Pat. No. 3,822,254 issued July 2, 1974.

In the first step of the synthetic sequence, the 24,25-double bond of a compound of formula I is hydroxylated to a mixture of compounds of the formulas

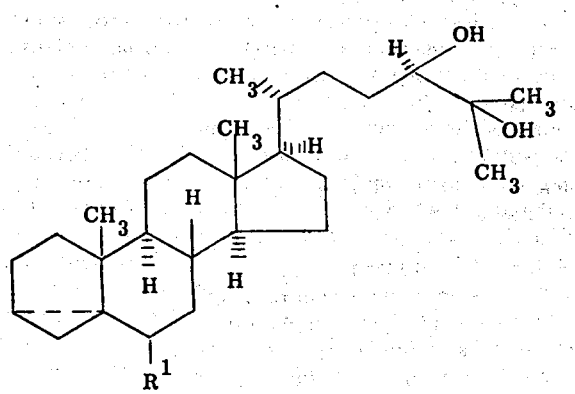

and

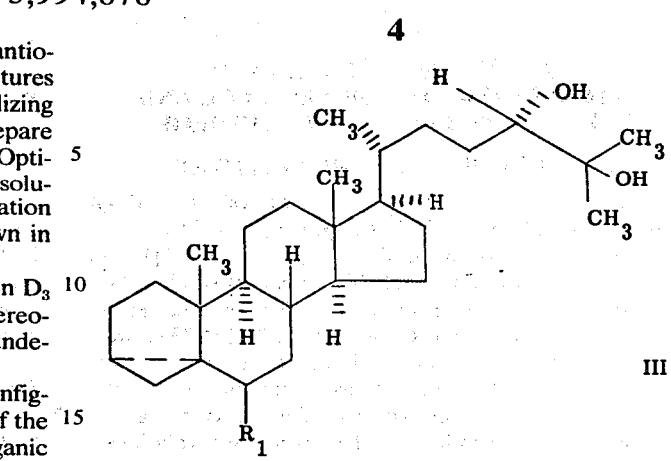

III wherein
$R_1$ is as above and the absolute configuration of the C-24 hydroxyl group is R in the compound of formula II and
S in the compound of formula III
and the mixture is separated into its components by fractional crystallization or high pressure liquid chromatography.

The transformation is conveniently performed by treating a compound of formula I with osmium tetroxide in a suitable inert organic solvent at ordinary temperature followed by reductive hydrolysis of the resulting osmate ester by means of water and a suitable reducing agent added to the original solution at a slightly elevated temperature.

As suitable inert organic solvents there may be mentioned nitrogen-containing heteroaromatic solvents such as pyridine, lutidine and collidine, ethereal solvents such as diethyl ether, tetrahydrofuran and dioxane and aromatic solvents such as benzene, toluene and xylene. Nitrogen-containing heteroaromatic solvents are preferred. Pyridine is most preferred.

It is most convenient to perform the osmation step in the absence of light.

While the temperature of the osmation reaction is not narrowly critical, it is desirable to carry out this reaction at a temperature from about 0° C. to about 50° C., most desirably at a temperature of about 25° C. Similarly, the temperature at which the reductive hydrolysis of the osmate ester is performed is not narrowly critical. A slightly elevated temperature within the range of about 30° C. to 50° C. is preferred. A reductive hydrolysis temperature of about 40° C. is most preferred.

Among suitable reducing agents are alkali metal sulfites and bisulfites such as sodium or potassium sulfite or bisulfite and the like, and hydrogen sulfide. Hydrogen sulfide is preferred. Sodium bisulfite is most preferred. Sugars such as mannitol are also useful to effect the cleavage of the osmate ester.

The initial separation of the stereoisomeric diols of formulas II and III is accomplished by means of high pressure liquid chromatography employing a solid absorbent column and an inert organic solvent. Suitable inert organic solvents for the separation step include mixtures of hydrocarbons such as n-hexane, isooctane, benzene, toluene and the like and esters such as ethyl acetate, ethyl benzoate and the like. Suitable solid absorbents include Porasil, Corasil, Biosil, Zorbax, Zorbax-Sil, Sil-X and the like. A Waters Associates Chromatograph Model 202 using a 8 foot by ⅜ inch Porasil A column and a mixture of n-heptane/diethyl ether as the eluent is the preferred high pressure liquid chromatographic system.

In subsequent steps of the reaction sequence each isomeric diol of formulas II and III is separately converted to the final isomeric i-steroidal epoxides by conversion of the C-24 hydroxy groups to the corresponding lower alkyl- or lower alkylphenylsulfonyloxy derivative followed by cyclization.

For example, the i-steroidal diol of formula II wherein the stereochemistry at C-24 is R is readily converted to a compound of the formula

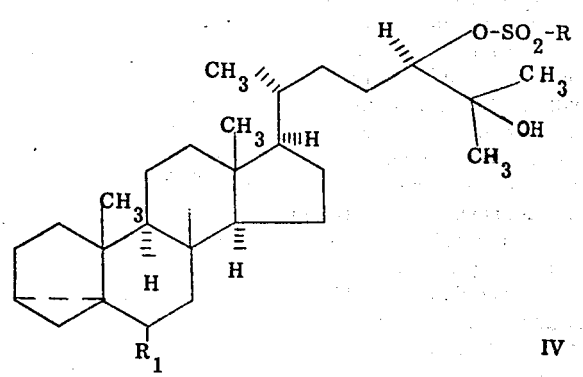

IV wherein $R_1$ is as above and $R_2$ is lower alkyl or lower alkylphenyl and the absolute stereochemistry is R and subsequently cyclized with inversion of configuration at C-24 to a compound of the formula

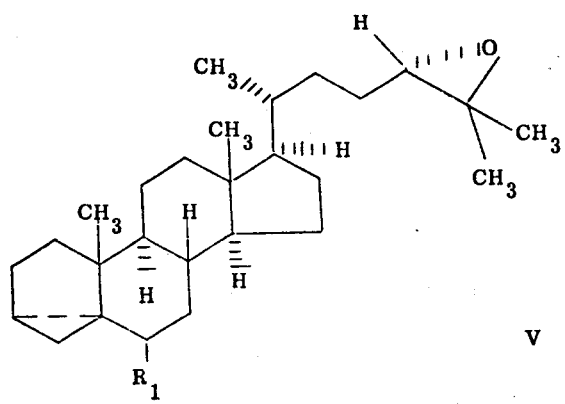

V wherein $R_1$ is as above and the absolute configuration at C-24 is S.

The sulfonylation is conveniently carried out by treating a compound of formula II with a lower alkyl- or lower alkylphenylsulfonyl halide, lower alkyl- or lower alkylphenylsulfonic acid anhydride of the formula

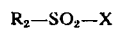

$R_2-SO_2-X$     VI wherein X is bromo, chloro or $R_2SO_2$ and $R_2$ is as above in a suitable solvent medium comprising an organic solvent and an organic acid acceptor at a reduced reaction temperature.

Among suitable organic solvents there may be mentioned aromatic solvents such as benzene, toluene, xylene and the like and heteroaromatic solvents, particularly nitrogen containing heteroaromatic solvents such as pyridine, picoline, lutidine, collidine and the like. Among suitable organic acid acceptors there may be mentioned acyclic aliphatic amines such as triethylamine, tripropylamine and the like, alicyclic aliphatic amines such as 1,4-diazobicyclo[2.2.2]octane, 1,5-diazabicyclo[3.4.0]non-5-ene and the like, aliphatic aromatic amines such as dimethyl and diethylaniline and the like and heteroaromatic amines such as pyridine, picoline, lutidine, collidine and the like. It is preferred to employ the same heteroaromatic amine as the organic solvent and acid acceptor. It is most preferred to use pyridine as both the solvent and acid acceptor.

Since the C-24 sulfonyloxy group is displaced in the next step of the reaction sequence, the structure of the $R_2$ moiety of the leaving group is not critical. Nevertheless, it is preferred to employ a sulfonyloxy i-steroid wherein $R_2$ is lower alkyl or lower alkylphenyl, and it is most preferred to employ the compound wherein $R_2$ is methyl. Accordingly, sulfonylating agents of formula VI wherein $R_2$ is lower alkyl or lower alkylphenyl and X is chloro or methanesulfonyloxy are preferred. Methanesulfonyl chloride is most preferred.

To prevent side reactions such as sulfonylation and/or dehydration of the C-25 hydroxy group, it is preferred to effect the derivatization of the C-24 hydroxy group at a reduced temperature of about $-25°$ C. to about $25°$ C. The most preferred reaction temperature is about $0°$ C.

While the molar ratio of sulfonylating agent of formula VI to i-steroidal diol of formula II is not critical, it is preferred to use a molar ratio of about 10:1. A molar ratio of about 6:1 is most preferred.

The cyclization step is readily performed by treating a compound of formula IV with a metal hydride in a suitable organic solvent at a reduced temperature of about $-25°$ C. to about $25°$ C., a reaction temperature of about $0°$ C. being preferred.

Suitable organic solvents for the cyclization process step include ethereal solvents such as diethyl ether, dimethoxyethane, tetrahydrofuran and dioxane and the like, and aromatic solvents such as benzene, dimehtoxyethoxyethane, toluene, xylene and the like. Ethereal solvents are preferred. Tetrahydrofuran is most preferred.

Metal hydrides suitable for the cyclization reaction include, among others, alkali metal hydrides such as sodium hydride, potassium hydride and the like. Sodium hydride is preferred. Sodium hydride oil emulsion is most preferred.

Similarly, the isomeric diol of formula III wherein the stereochemistry at C-24 is S may be converted to the C-24 sulfonyloxy derivative of the formula

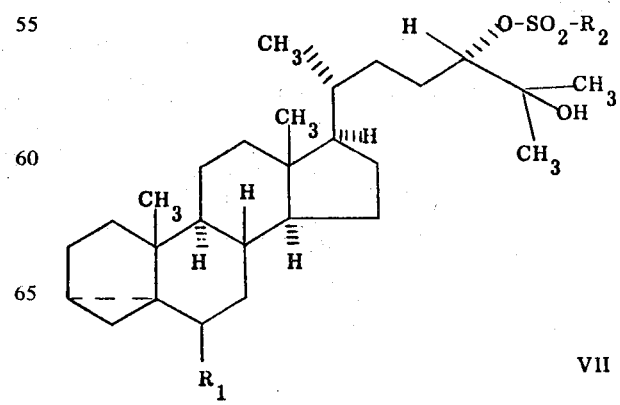

VII wherein
R₁ and R₂ are as above and the absolute configuration at C-24 is S and cyclized to a compound of the formula

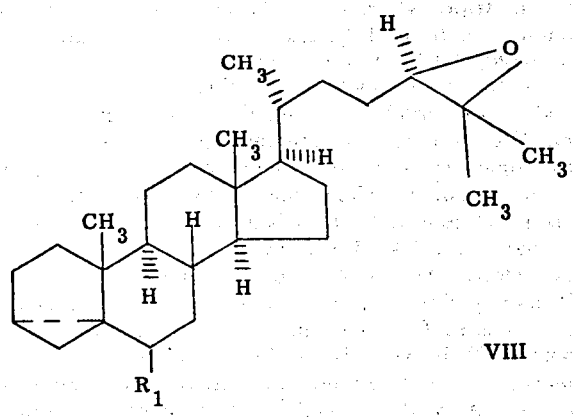

VIII wherein
R₁ is as above and the absolute configuration at C-24 is R with inversion at C-24.

Alternatively, the C-24R- and S-epoxides of formulas VIII and V, respectively, can be synthesized by epoxidation of a compound of formula I with an organic peracid according to the method described in U.S. Pat. No. 3,822,254 followed by separation of the mixture of epimers by fractional crystallization, a method well-known in the art.

To complete the synthesis of 24R,25- and 24S,25-dihydroxycholesterol and alkanoyl derivatives thereof of the formula

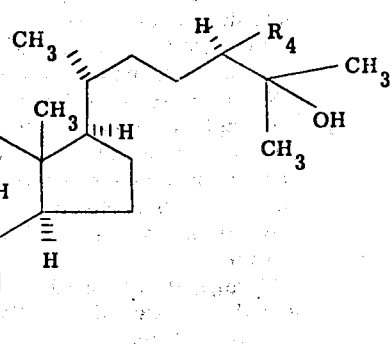

IX wherein
R₃ and R₄ are hydroxy or lower alkanoyloxy and the absolute configuration at C-24 is R
and the formula

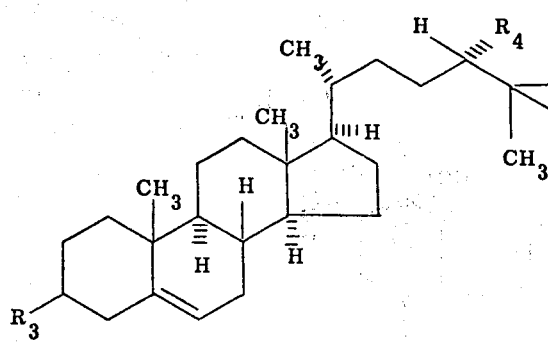

X wherein
R₃ and R₄ are hydroxy or lower alkanoyloxy and the absolute configuration at C-24 is S
the R- and S-epoxides of formulas VIII and V, respectively, can be either directly converted to the cholesterols of formulas IX and X or selectively cleaved first to the i-steroidal diols of the formulas II and III.

The step-wise cleavage, that is, the selective cleavage of the epoxy group of compounds of formulas VIII and V without retro-i-rearrangement, followed by retro-i-steroid rearrangement to cholesterols of formulas IX and X wherein R₃ and R₄ are hydroxy is accomplished by first treating epoxides of formulas VIII and V with a strong acid in a solvent medium comprising water and an inert organic water miscible solvent at a reduced temperature, isolating the unrearranged i-steroidal diols of formulas II and III and then treating the latter with a strong acid in an inert organic solvent at an elevated temperature.

For these cleavage reactions, the epoxy to diol reaction and the retro-i-steroid rearrangement, strong mineral acids such as hydrochloric, hydrobromic, sulfuric acid and the like, and organic sulfonic acids such as methanesulfonic acid, benzenesulfonic acid, p-toluenesulfonic acid and the like are suitable. Sulfruic acid and organic sulfonic acids are preferred. Sulfuric acid is most preferred.

Included among suitable water miscible organic solvents are ethereal solvents such as dimethoxyethane, diethoxyethoxyethane, tetrahydrofuran and dioxane. Tetrahydrofuran and dioxane are the preferred solvents. Tetrahydrofuran is the most preferred solvent for the selective epoxy cleavage reaction and dioxane is the most preferred solvent for the epoxy cleavage-retro-i-steroid rearrangement sequence.

To avoid concommitant retro-i-steroid rearrangement during cleavage of the epoxy group, the reaction should be maintained at a reduced temperature of about −20° to +10° C. An especially preferable temperature range is from about −10° to about +5° C., most preferably about 0° C.

To promote retro-i-steroid rearrangement during cleavage of the epoxy group, the reaction should be performed at an elevated temperature of about +40° C. to about 100° C. A reaction temperature within the range of about 50° C. to about 90° C. is especially preferred, a reaction temperature of about 80° C. being most preferred.

If one desires to prepare cholesterols of formulas IX and X wherein $R_3$ and $R_4$ are lower alkanoyloxy by cleavage of the epoxy group with concurrent retro-i-steroid rearrangement, the reaction is carried out in a reaction medium containing the alkanoic acid corresponding to the desired alkanoyloxy group at an elevated temperature. For example, to prepare cholesterols of formulas IX and X wherein $R_3$ and $R_4$ are acetoxy, one employs acetic acid as the solvent medium and a temperature within the above stated range of about 40° to about 100° C. A reaction temperature from about 50° to about 90° C. is preferred, a reaction temperature of about 80° C. being particularly preferred. Since the lower alkanoic acid is a sufficiently strong acid to catalyze both the epoxide cleavage reaction and the retro-i-steroid rearrangement, a strong acid need not be added to the reaction medium. It is advantageous to use an alkali metal salt of the lower alkanoic acid, such as sodium or potassium acetate for the above-mentioned example, to promote both cleavage reactions.

The 24R, 25 and 24S, 25-dihydroxycholesterols of formulas IX and X and their lower alkanoyl derivatives can be interconverted, that is, the dihydroxycholesterols can be alkanoylated to the 3,24-di-(alkanoyloxy) derivatives and the alkanoyl derivatives can be hydrolyzed to the cholesterols, by methods well-known in the art. For example, to acetylate the 3- and 24-hydroxy groups of cholesterols of formulas IX and X, one employs acetic anhydride pyridine at a temperature of about 25° C, and to saponify the 3- and 24-acetyl groups of the cholesterol derivatives of formulas IX and X, one employs an alkali metal hydroxide such as sodium or potassium hydroxide in a lower alkanol such as methanol, ethanol and the like at a temperature of about 25° C.

24R, 25 and 24S, 25-dihydroxycholesterol and the alkanoyl derivatives thereof are useful intermediates for the preparation of the C-24 stereoisomers of the biologically important metabolite of vitamin $D_3$, 24R, 25-dihydroxycholecalciferol by routes well-known in the art, and the unnatural 24S stereoisomer. This transformation is accomplished by introduction of the $\Delta^7$- double bond, generally by a halogenation-dehydrohalogenation process, followed by photolysis of the diene and thermal isomerization of the previtamin, and hydrolysis of the alkanoyl groups, if necessary. See, for example, J. Redal et al., supra, and H. Y. Lam et al., supra.

The following examples are illustrative of the invention and are not to be construed as limiting the invention in any manner.

EXAMPLE 1

24R- and 24S, 25-Dihydroxy-6β-methoxy-3α,5-cyclo-5α-cholestane.

To a solution of 6β-methoxy-3α,5-cyclo-5α-cholest-24-ene (1.49 g, 0.0037 mole) and dry pyridine (20 ml) was added a solution of osmium tetroxide (1.00 g, 0.0039 mole) in pyridine (10 ml) and the mixture was stirred at 25° for 20 hours in the dark. A solution of sodium bisulfite (1.66 g, 0.0160 mole) in water (25 ml) was added and the mixture was stirred at 40° for 3 hours. The reaction mixture was diluted with water (100 ml) and extracted with ethyl acetate (3 × 100 ml). The combined organic extracts were washed with 10% aqueous sulfuric acid (2 × 100 ml), saturated aqueous sodium bicarbonate solution (2 × 100 ml) and saturated sodium chloride solution (2 × 100 ml). The organic layer was dried over anhydrous magnesium sulfate and the drying agent was collected on a filter. Evaporation of the filtrate gave 1.40 g (87%) of a 1:1 mixture of diols.

The reaction product was separated on a Waters Associate Chromatography Model 202 using an 8 ft by ⅜ in Porasil A: and a misture of n-heptone-ethyl ether.

In a second experiment using the same reaction conditions, the 1:1 mixture of diols was dissolved in hot benzene and seeded with previously prepared authentic 24S,25-dihydroxy-6β-methoxy- -3α,5-cyclo-5α-cholestane to give 0.60 g (37%) of pure 24S-isomer, m.p. 167°–168°.

$[\alpha]_D^{25}$ + 39.0° (c 1.04, $CHCl_3$).

The benzene filtrate was evaporated and the residue was dissolved in hot ethyl acetate and seeded with authentic 24R,25-dihydroxy-6β-methoxy-3α,5-cyclo-5α-cholestane to give 0.54 g (33%) of pure 24R-isomer, m.p.142°–143°.

$[\alpha]_D^{25}$+63.2° (c 1.11, $CHCl_3$).

EXAMPLE 2

25-Hydroxy-6α-methoxy-24R-methylsufonyloxy-3α,5-cyclo-5α- -cholestane.

To a solution of 24R,25-dihydroxy-6β-methoxy-3α,5- -cyclo-5α-cholestane (0.050 g, 0.000116 mole) in dry pyridine (0.5 ml) cooled to 0° was added methanesulfonyl chloride (0.05 ml, 0.00066 mole) and the reaction mixture was stirred at 0° for 0.5 hour. Ice (0.10 g) was added to destroy excess methanesulfonyl chloride and the mixture was stirred briefly. The solution was washed with 10% aqueous sulfuric acid (2 × 10 ml) and saturated aqueous sodium bicarbonate solution (2 × 10 ml). The organic layer was dried over anhydrous magnesium sulfate and after removal of the drying agent by filtration, the filtrate was evaporated to dryness to yield 0.059 g (100%) of 25-hydroxy-6β-methoxy-24R-methylsulfonyloxy-3α,5-cyclo-5αcholestane.

$[\alpha]_D^{25}$ + 44.7° (c 1.03, $CHCl_3$).

EXAMPLE 3

25-Hydroxy-6β-methoxy-24S-methylsulfonyloxy-3α,5-cyclo-5α-cholestane.

25-Hydroxy-6β-methoxy-24S-methylsulfonyloxy-3α,5- -cyclo-5α-cholestane was prepared in 100% yield according to the procedure of Example 2.

$[\alpha]_D^{25}$ + 39.5° (c 0.80, $CHCl_3$).

EXAMPLE 4

24s,25-Epoxy-6 β-methoxy-3α,5-cyclo-5α-cholestane. To a suspension of sodium hydride (0.024 g, 0.0010 mole) in tetrahydrofuran (1 ml) cooled to 0° was added dropwise a solution of 25-hydroxy-6β-methoxy-24R-methylsulfonyloxy-3α,5-cyclo-5α-cholestane (0.059 g, 0.000116 mole) in tetrahydrofuran (0.5 ml), with stirring. After 0.5 hours, the reaction mixture was diluted with water (10 ml) and the solution was extracted with methylene chloride (3 × 10 ml). The combined organic extracts were washed with water (2 × 10 ml), dried over anhydrous magnesium sulfate, filtered and evaporated to dryness. Recrystallization of the solid residue from methyl ethyl ketone gave 0.041 g (91%) of 24S, 25-epoxy-6β-methoxy-3α,5-cyclo- 5α-cholestane, m.p. 100°–102°.

$[\alpha]_{D25} + 42.2°$ (c 0.97, $CHCl_3$).

EXAMPLE 5

24R,25-Epoxy-3α,5-cyclo-5α-cholestane.

24R,25-Epoxy-3α,5-cyclo-5αcholestane was prepared in 93% yield from 25-hydroxy- -6β-methoxy-24S-methylsulfonyloxy-3α,5-cyclo-5α-cholestane according to the procedures of Example 4, m.p. 126°–127°.

$[\alpha]_D^{25} + 58.0°$ (c 1.08, $CHCl_3$).

EXAMPLE 6

24S,25-Dihydroxy-6β-methoxy-3α,5-cyclo-5α-cholestane.

A solution of 24S,25-epoxy-6β-methoxy-3α,5-cyclo-5α-cholestane (0.200 g, 0.00049 mole), tetrahydrofuran (8 ml) and 1.0N aqueous sulfuric acid (2 ml) was stirred at 0° for 3 hours. The reaction mixture was diluted with water (25 ml) and extracted with methylene chloride (3 × 25 ml). The combined organic layers were washed with saturated aqueous sodium bicarbonate solution (25 ml), dried over anhydrous magnesium sulfate, filtered and evaporated. Recrystallization of the residue from benzene gave 0.153 g (73%) of 24S,25-dihydroxy-6β-methoxy-3α,5-cyclo-5α-cholestane, m.p. 167°–168°.

$[\alpha]_D^{25} + 38.7°$ (c 0.96, $CHCl_3$).

Anal. Calcd for $C_{28}H_{48}O_3$ (MW 432.69): C, 77.73; H, 11.18; Found: C, 77.97; H, 10.94.

EXAMPLE 7

24R,25-Dihydroxy-6β-methoxy-3β,5-cyclo-5αcholestane.

A solution of 24R,25-epoxy-6β-methoxy-3α,5-cyclo-5α-cholestane (0.104 g, 0.00025 mole), tetrahydrofuran (8 ml) and 1N aqueous sulfuric acid (2 ml) was stirred at 0° for 4 hours. Water (25 ml) was added to the reaction mixture and the solution was extracted with methylene chloride (3 × 25 ml). The combined organic layers were washed with saturated aqueous sodium bicarbonate solution (25 ml), dried over anhydrous magnesium sulfate, filtered and evaporated. Recrystallization of the residue from ethyl acetate afforded 0.090 g (83%) of 24R,25-dihydroxy-6β-methoxy-3α,5-cyclo- 5α-cholestane, m.p. 142°–143°.

$[\alpha]_D^{25} + 63.0°$ (c 1.08, $CHCl^3$).

Anal. Calcd. for $C_{28}H_{48}O_3$ (MW 432.69): C, 77.73; H, 11.18; Found: C, 77.49; H, 11.07.

EXAMPLE 8

24R,25- and 24S,25-Epoxy-6β-methoxy-3α,5-cyclo-5α-cholestane.

A mixture of 6β-methoxy-3α,5-cyclo-5α-cholest-24-ene (5.00 g, 0.0126 mole), methylene chloride (75 ml) and sodium bicarbonate (6.00 g) was cooled to 0° and m-chloroperbenzoic acid of 85% purity by weight (2.81 g, 0.0138 mole) was added, with stirring. The reaction mixture was stirred at 0° for 1 hour and at room temperature for 16 hours. The mixture was then diluted with water (75 ml) and extracted with ethyl acetate (3 × 75 ml). The ethyl acetate extract was washed with 10% aqueous sodium hydroxide solution (75 ml), water (75 ml) and saturated sodium choloride solution (75 ml). The extract was dried over anhydrous magnesium sulfate, filtered and evaporated to dryness to yield 4.88 g (94%) of a 55:45 mixture of the 24R- and 24S-isomers as determined by high pressure liquid chromatography utilizing the procedure described in Example 1. Fractional crystallization of the mixture from acetone gave 2.30 g of 24R,25-epoxy-6β-methoxy-3α,5-cyclo- -5α-cholestane, m.p. 126°–127°.

$[\alpha]_D^{25} + 58.1°$ (c 1.10, $CHCl_3$)

Anal. Calcd. for $C_{28}H_{46}O_2$ (MW 414.68): C, 81.10; H, 11.18; Found: C, 81.17; H, 11.13.

Recrystallization of the residue obtained by evaporation of the mother liquors from methyl ethyl ketone gave 1.80 g of 24S,25-epoxy-6β-methoxy-3α,5-cyclo-5α-cholestane, m.p. 100°–102°.

$[\alpha]_D^{25} + 42.6°$ (c 1.03, $CHCl_3$).

Anal. Calcd. for $C_{28}H_{46}O_2$ (MW 414.68): C, 81.10; H, 11.18; Found: C, 81.07; H, 11.13.

EXAMPLE 9

24R,25-Dihydroxycholesteryl 3,24-diacetate.

A solution of 24R,25-epoxy-6β-methoxy-3α,5-cholestane (0.415 g, 0.0010 mole) in 1.0M sodium acetate in acetic acid (8 ml) was heated at 60°–65° for 18 hours. The reaction mixture was cooled and diluted with methylene chloride (75 ml). The solution was washed with water (50 ml), saturated aqueous sodium bicarbonate solution (50 ml) and dried over anhydrous magnesium sulfate. The drying agent was collected and the filtrate was evaporated to dryness to yield 0.450 g of a solid residue. Recrystallization of the residue from hexane gave 0.395 g (79%) of 24R,25-dihdroxy- cholesteryl 3,24-diacetate, m.p. 122°–123°.

$[\alpha]_D^{25} - 37.7°$ (c 1.08, $CHCl_3$).

Anal. Calcd. for $C_{32}H_{50}O_4$ (MW 502.74): C, 74.06; H, 10.03; Found: C, 74.19; H, 10.22.

EXAMPLE 10

24R,25-dihdroxycholesterol.

A mixture of 24R,25-epoxy-6β-methoxy-3α,5-cyclo-5α-cholestane (0.415 g, 0.0010 mole), 0.1N aqueous sulfuric acid (1.0 ml) and dioxane (5 ml) was heated at 80° for 4 hours and then allowed to cool. Water (10 ml) was added to the reaction mixture and the precipitate was collected by filtration. The wet solid was dissolved in methylene chloride (50 ml) and the solution was washed with saturated aqueous sodium bicarbonate solution (2 × 25 ml) and dried over anhydrous magnesium sulfate. Filtration of the drying agent followed by evaporation of the filtrate to dryness and recrystallization of the residue from methanol gave 0.34 (81%) of 24R,25-dihydroxy- cholesterol, m.p. 200°–202°.

$[\alpha]_D^{25} - 12.0°$ (c 1.13, $CH_3OH$).

EXAMPLE 11

24S,25-Dihydroxycholesteryl 3,24-diacetate.

A solution of 24S,25-epoxy-6β-methoxy-3α,5-cyclo-5α-cholestane (0.550 g, 0.00133 mole) in 1.0 M sodium acetate in acetic acid (6 ml) was heated 60°–65° for 18 hours. The reaction mixture was cooled and diluted with methylene chloride (75 ml). The solution was washed with water (50 ml) and saturated aqueous sodium bicarbonate solution (50 ml), dried over anhydrous magnesium sulfate and filtered. Evaporation of the filtrate followed by recrystallization of the residue from ether-hexane afforded 0.415 g (62%) of 24S,25-dihydroxycholesteryl 3,24-diacetate, m.p. 174°–175°.

$[\alpha]_D^{25} - 41.0°$ (c 0.98, $CHCl_3$).

Anal. calcd. for $C_{31}H_{50}O_4$ (MW 502.74): C, 74.06; H, 10.03; Found: C, 74.05; H, 9.82.

EXAMPLE 12

24S, 25-Dihydroxycholesterol.

A mixture of 24S,25-epoxy-6β-methoxy-3α,5-cyclo-5α-cholestane (0.208 g, 0.00050 mole), 0.1N aqueous sulfuric acid (0.5 ml) and dioxane (3 ml) was heated at 80° for 4 hours and allowed to cool. Water (5 ml) was added to the reaction mixture and the precipitate was collected by filtration. The solid was dissolved in methylene chloride (35 ml) and the solution was washed with saturated aqueous sodium bicarbonate solution (2 × 15 ml), dried over anhydrous magnesium sulfate, filtered and evaporated to dryness. Recrystallization of the solid residue from methanol gave 0.165 g (79%) of 24S,25-dihydroxycholesterol, m.p. 196°–198°.

$[\alpha]_D^{25} - 45.7°$ (c 1.00, $CH_3OH$).

EXAMPLE 13

24R,25-Dihydroxycholesterol.

A mixture of 24R,25-dihydroxy-cholesteryl 3,24-diacetate (0.252 g, 0.0005 mole), sodium hydroxide (0.200 g, 0.0050 mole) and methanol (6.0 ml) was stirred at 25° for 16 hours. Water (75 ml) was added to the reaction mixture and the solution was extracted with methylene chloride 2 × 75 ml). The organic extracts were washed with water (22 ×75 ml), dried over anhydrous magnesium sulfate, filtered and concentrated to dryness. Recrystallization of the residue from methanol afforded 0.174 g (83%) of 24R,25-dihydroxycholesterol, m.p. 200°–202°.

$[\alpha]_D^{25} - 11.3°$ (c 1.02, $CH_3OH$).

Anal. Calcd. for $C_{27}H_{46}O_3$ (MW 418.67): C, 77.46; H, 11.07; Found: C, 77.18; H, 11.19.

EXAMPLE 14

24R,25-Dihydroxycholesteryl 3,24-diacetate.

A solution of 24R,25-dihydroxycholesterol (0.420 g, 0.0010 mole), acetic anhydride (0.408 g, 0.0040 mole) and dry pyridine (4 ml) was stirred for 16 hours at 25°. Ice (0.50 g) was added to the reaction mixture and the mixture was stirred briefly and then added to methylene chloride (50 ml). The solution was washed with 10% aqueous sulfuric acid (2 × 25 ml) and saturated aqueous sodium bicarbonate solution (2 × 25 ml), dried over anhydrous magnesium sulfate and filtered. Evaporation of the filtrate followed by recrystallization of the residue gave 0.452 (90%) of 24R,25-dihydroxycholesteryl 3,24-diacetate, m.p. 122°–123°.

$[\alpha]_D^{25} - 37.8°$ (c 1.06, $CHCl_3$).

EXAMPLE 15

24S,25-Dihydroxycholesterol.

24S,25-Dihydroxycholesterol was prepared in 79% yield from 24S,25-dihydroxycholesteryl 3,24-diacetate (0.125 g, 0.00025 mole), sodium hydroxide (0.100 g, 0.00250 mole) and methanol (3 ml); m.p. 196°–198°.

$[\alpha]_D^{25} - 46.1°$ (c 0.98, $CH_3OH$).

Anal. Calcd. for $C_{27}H_{46}O_3$ (MW 418.67): C, 77.46; H, 11.07; Found: C, 77.29; H, 10.89.

EXAMPLE 16

24S,25-Dihydroxycholesteryl 3,24-diacetate.

24S,25-Dihydroxycholesteryl 3,24-diacetate was prepared in 91% yield from 24S,25-dihydroxycholesterol (0.102 g, 0.00024 mole), acetic anhydride (0.102 g, 0.0010 mole) and dry pyridine (2 ml) according to the procedure described for the corresponding 24R-isomer given in Example 14, m.p. 173°–174°.

$[\alpha]_D^{25} - 41.2°$ (c 1.02, $CHCl_3$).

We claim:

1. A process for the preparation of a compound of the formula

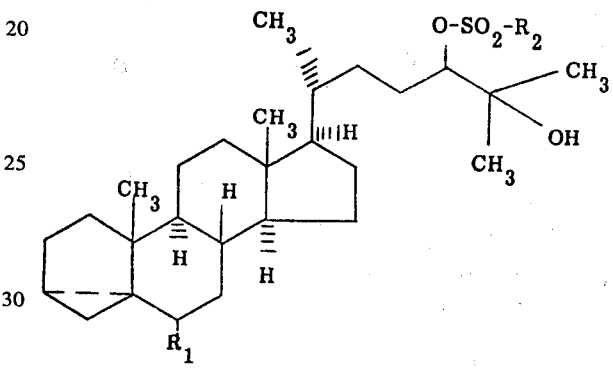

wherein
$R_1$ is hydroxy, lower alkoxy, phenyl lower alkoxy, lower alkanoyloxy or benzoyloxy and
$R_2$ is lower alkyl or lower alkyl phenyl
which comprises contacting a compound of the formula

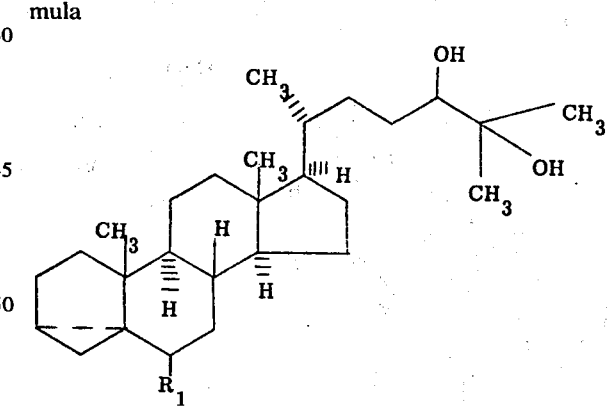

wherein
$R_1$ is as above with a compound of the formula
$R_2-SO_2-X$
wherein
X is chloro, bromo or $R_2SO_2O$ and $R_2$ is lower alkyl or lower alkylphenyl
in a solvent medium comprising an organic solvent and an acid acceptor.

2. The process of claim 1 wherein $R_1$ is alkoxy.

3. The process of claim 2 wherein $R_1$ is methoxy.

4. The process of claim 1 wherein the configuration of the C-24 hydroxyl group is R.

5. The process of claim 1 wherein the configuration of the C-24 hydroxyl group is S.

6. The process of claim 1 wherein the configuration of the C-24 sulfonyloxy group is R.

7. The process of claim 1 wherein the configuration of the C-24 sulfonyloxy group is S.

8. The process of claim 1 wherein $R_2$ is lower alkyl.

9. The process of claim 8 wherein $R_2$ is methyl.

10. The process of claim 1 wherein $R_2$ is lower alkyphenyl.

11. The process of claim 10 wherein $R_2$ is 4-tolyl.

12. The process of claim 1 wherein X is chloro or $R_2SO_2O$.

13. The process of claim 12 wherein X is $R_2SO_2O$.

14. The process of claim 1 wherein the organic solvent and the acid acceptor are the same heteroaromatic compound.

15. The process of claim 14 wherein the heteroaromatic compound is pyridine.

16. A process for the preparation of a compound of the formula

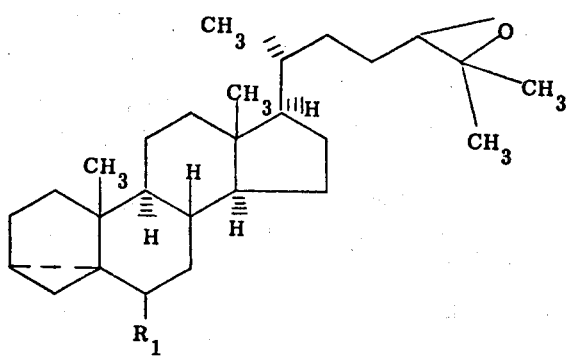

wherein
$R_1$ is hydroxy, lower alkoxy, phenyl lower alkoxy, lower alkanoyloxy or benzoyloxy
which comprises contacting a compound of the formula

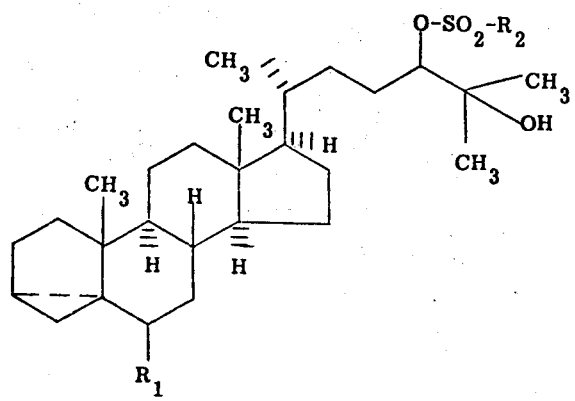

wherein
$R_1$ is as above and $R_2$ is lower alkyl or lower alkylphenyl, with a metal hydride in an inert solvent at a reduced temperature.

17. The process of claim 16 wherein $R_1$ is lower alkoxy.

18. The process of claim 17 wherein $R_1$ is methoxy.

19. The process of claim 16 wherein the absolute configuration of the epoxy group is 24S.

20. The process of claim 16 wherein the absolute configuration of the epoxy group is 24R.

21. The process of claim 16 wherein $R_2$ is lower alkyl.

22. The process of claim 21 wherein $R_2$ is methyl.

23. The process of claim 16 wherein $R_2$ is lower alkylphenyl.

24. The process of claim 23 wherein $R_2$ is 4-tolyl.

25. The process of claim 16 wherein the metal hydride is an alkali metal hydride.

26. The process of claim 25 wherein the alkali metal hydride is sodium hydride.

27. The process of claim 16 wherein the inert solvent is an ethereal solvent.

28. The process of claim 27 wherein the ethereal solvent is tetrahydrofuran.

29. The process of claim 16 wherein the temperature is $-25°$ C. to $+25°$ C.

30. The process of claim 29 wherein the temperature is about 0° C.

31. A process for the preparation of a compound of the formula

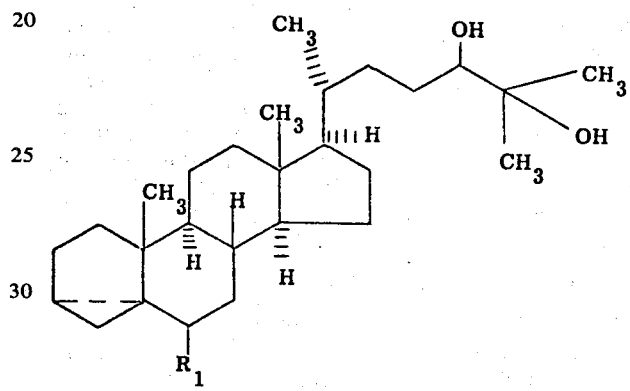

wherein
$R_1$ is hydroxy, lower alkoxy, phenyl lower alkoxy, lower alkanoyloxy or benzoyloxy
which comprises contacting a compound of the formula

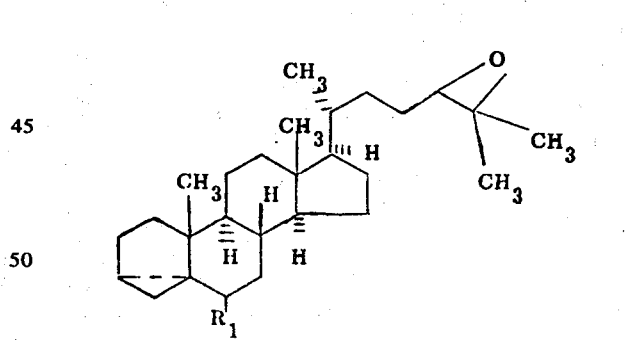

wherein
$R_1$ is as above with sulfuric acid or an organic sulfonic acid in an aqueous solvent medium at a reduced temperature.

32. The process of claim 31 wherein $R_1$ is lower alkoxy.

33. The process of claim 32 wherein $R_1$ is methoxy.

34. The process of claim 31 wherein the absolute configuration at C-24 is R.

35. The process of claim 31 wherein the absolute configuration at C-24 is S.

36. The process of claim 31 wherein the organic sulfonic acid is 4-toluene sulfonic acid monohydrate.

37. The process of claim 31 wherein the reduced temperature is $-25°$ C. to $+25°$ C.

38. The process of claim 36 wherein the reduced temperature is about 0° C.

39. The process of claim 31 wherein the aqueous solvent medium comprises a miscible ethereal solvent.

40. The process of claim 39 wherein the miscible ethereal solvent is tetrahydrofuran.

41. The process of claim 40 wherein the miscible ethereal solvent is dioxane.

42. A compound of the formula

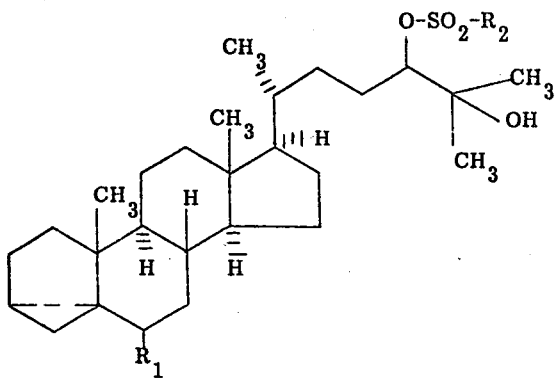

wherein
R₁ is hydroxy, lower alkoxy, phenyl lower alkoxy, lower alkanoyloxy or benzolyloxy and R₂ is lower alkyl or lower alkyl phenyl.

43. The compound of claim 42 wherein R₁ is lower alkoxy, R₂ is lower alkyl and the absolute configuration at C-24 is R or S.

44. The compound of claim 43 which is 25-hydroxy-6β-methoxy-24S-methylsulfonyloxy-3α,5-cyclo-5α-cholestane.

45. The compound of claim 43 which is 25-hydroxy-6β-methoxy-24R-methylsulfonyloxy-3α,5-cyclo-5α-cholestane.

* * * * *